(12) United States Patent
Otsuka et al.

(10) Patent No.: US 8,317,803 B2
(45) Date of Patent: Nov. 27, 2012

(54) SURGERY EQUIPMENT HOLDING DEVICE

(75) Inventors: Satoshi Otsuka, Hachioji (JP); Toru Shinmura, Hachioji (JP); Kenji Omachi, Hachioji (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 13/329,936

(22) Filed: Dec. 19, 2011

(65) Prior Publication Data

US 2012/0089155 A1    Apr. 12, 2012

Related U.S. Application Data

(60) Continuation of application No. 11/635,713, filed on Dec. 7, 2006, now Pat. No. 8,100,919, which is a division of application No. 10/114,539, filed on Apr. 2, 2002, now Pat. No. 7,160,308.

(30) Foreign Application Priority Data

May 22, 2001    (JP) .................................. 2001-152922

(51) Int. Cl.
    *A61B 19/00*    (2006.01)
(52) U.S. Cl. ........................................ 606/130; 600/114
(58) Field of Classification Search ............... 606/79, 606/130, 166; 600/114, 166
    See application file for complete search history.

(56) References Cited

U.S. PATENT DOCUMENTS

| 4,863,133 A | 9/1989 | Bonnell |
| 5,271,384 A | 12/1993 | McEwen et al. |
| 5,506,912 A | 4/1996 | Nagasaki et al. |
| 5,779,623 A | 7/1998 | Bonnell |
| 5,836,869 A | 11/1998 | Kudo et al. |

FOREIGN PATENT DOCUMENTS

| DE | 295 11 899 U1 | 11/1995 |
| EP | 0 293 760 B1 | 12/1988 |
| JP | 7-227398 | 8/1995 |
| JP | 10-61312 | 3/1998 |
| JP | 2843507 | 10/1998 |

OTHER PUBLICATIONS

U.S. Official Action mailed Jul. 21, 2010 in corresponding U.S. Appl. No. 11/635,713.
U.S. Official Action mailed Jan. 5, 2011 in corresponding U.S. Appl. No. 11/635,713.
U.S. Official Action mailed May 12, 2011 in corresponding U.S. Appl. No. 11/635,713.

*Primary Examiner* — Victor Nguyen
(74) *Attorney, Agent, or Firm* — Scully, Scott, Murphy & Presser, P.C.

(57) ABSTRACT

A surgery equipment holding device including a holder for holding surgical equipment, a bar connected to the holder, a brake which operatively engages the bar for stopping movement of the bar, and a pair of switches for switching being an active state and an inactive state of the brake. The surgery equipment holding device is characterized in the operation thereof at the time of disengaging the fixation state, and exhibits excellent operability.

2 Claims, 15 Drawing Sheets

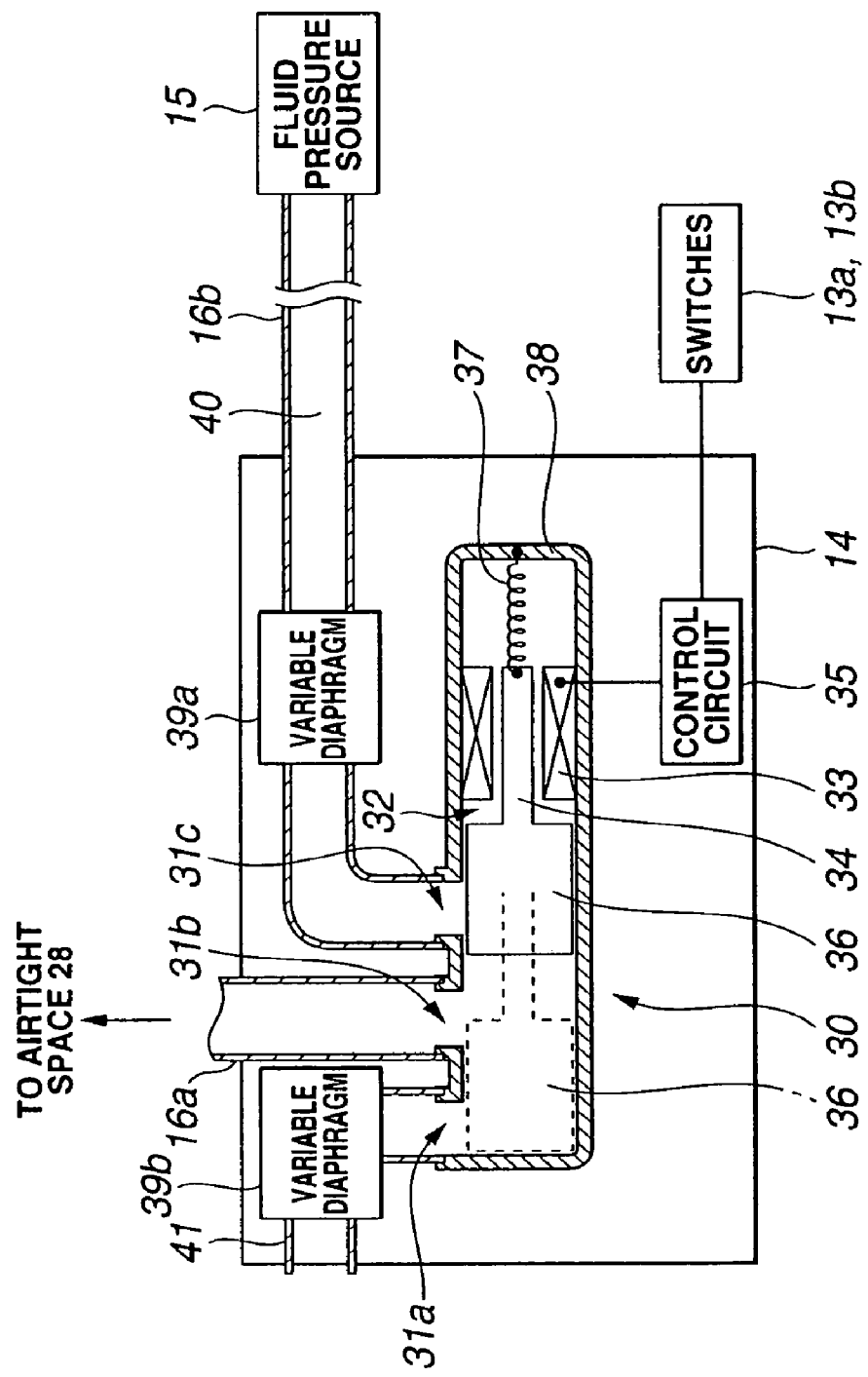

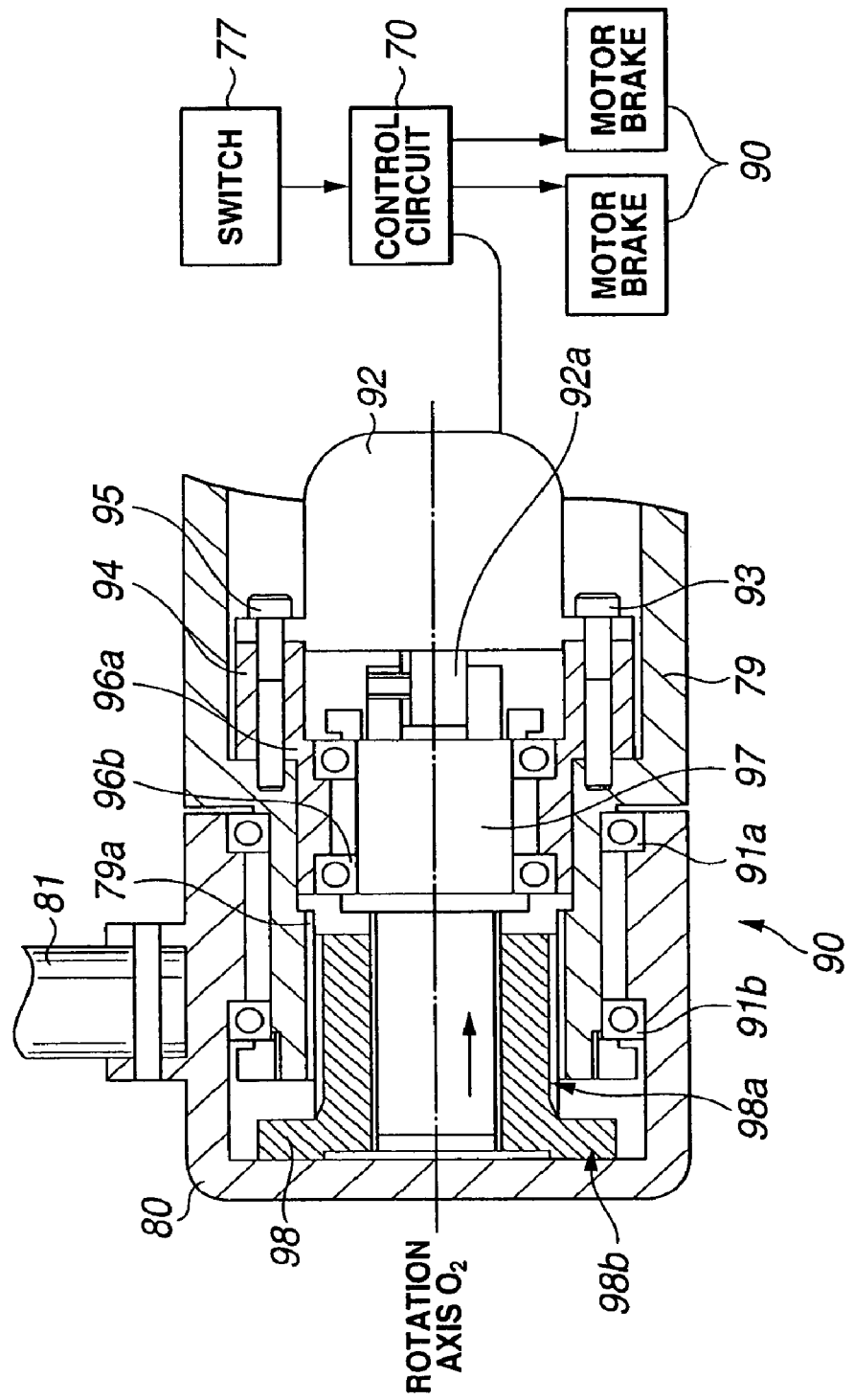

SURGERY EQUIPMENT HOLDING DEVICE

CROSS REFERENCE TO RELATED APPLICATIONS

This application is a continuation of U.S. patent application Ser. No. 11/635,713 filed on Dec. 7, 2006, which is a divisional of U.S. patent application Ser. No. 10/114,539 filed on Apr. 2, 2002, now U.S. Pat. No. 7,160,308, which claims the benefit of Japanese Patent Application No. 2001-152922 filed on May 22, 2001, the entire contents of each of which are incorporated herein by reference.

BACKGROUND OF THE INVENTION

1. Field of the Invention

The present invention relates to a surgery equipment holding device for holding surgery equipment, and particularly relates to a surgery equipment holding device with excellent operability, that is characterized in the operation thereof at the time of disengaging the fixation state.

2. Description of the Related Art

In recent years, surgery equipment holding devices which hold surgery equipment instead of surgeons have come into use. Such surgery equipment holding devices are configured having an arm portion serving as change holding means, joints serving as fixation maintaining means disposed at the arm portion, and switches serving as fixation disengaging instructing means.

Appropriately operating the switches changes the state of the joints between disengaged and fixed states. That is to say, moving the surgery equipment to a desired position and fixing it there can be performed by operating switches.

For example, DE 295 11 899 UI and Japanese Patent No. 2,843,507 have configurations wherein the fixed state of the joints is disengaged by a surgeon operating switches.

Also, the second embodiment disclosed in Japanese Unexamined Patent Application Publication No. 7-227398 discloses a surgery equipment holding device wherein the balance of an endoscope is maintained even in the event that the fixed state of the joints disposed on the arm portion is disengaged, by means of the surgery equipment holding device comprising an electromagnetic brake and counter balance.

Further, with the device for holding surgery equipment disclosed in EP 0 293 760 B1, two mode switches are provided. One mode switch is a first mode to immediately disengage the fixed state of the joints. The other mode switch is a second mode exhibiting a holding force wherein the joints disposed on the arm portion can hold an endoscope and also wherein the surgeon can move the endoscope.

However, with the surgery equipment holding devices disclosed in the aforementioned DE 295 11 899 UI and the aforementioned Japanese Patent No. 2,843,507, at the point that the surgeon operates switches to move the endoscope, the fixed state of the joints is immediately disengaged.

Accordingly, in the event that the surgeon operates switches to move the field of view of the endoscope, the fixed state is immediately disengaged, which suddenly places the weight of the endoscope and the arm portion onto the hand of the surgeon holding the endoscope. The surgeon is unable to respond to such sudden change of load and the tip of the endoscope undesirably moves. Accordingly, the surgeon loses the field of view prior to disengaging the fixation, and thus must perform the task of regaining the field of view. This has been a problem which has led to lowered surgery efficiency.

Also, with the surgery equipment holding device disclosed in the aforementioned Japanese Unexamined Patent Application Publication No. 7-227398, in the event that the surgeon operates switches, the fixed state of the joints is immediately disengaged. This suddenly places the force of the hand of the surgeon on the arm portion, and the same problem as described above occurs since the arm portion which is balanced is moved thereby.

Further, with the surgery equipment holding device disclosed in EP 0 293 760 B1, in the event that the surgeon specifies the second mode, the endoscope is held with a predetermined force, which takes care of the problem wherein the tip of the endoscope moves. However, with cases wherein the endoscope must be moved frequently during the surgery, such as with brain surgery for example, using this device causes the problem that the surgeon must move the endoscope against the resistance of the fixing force every time. This places a load on the hand and arm of the surgeon. Also, operations for moving the endoscope minute distances against the resistance of the fixing force have been difficult.

On the other hand, in the event that the surgeon specifies the first mode, the fixing force of the joints is immediately disengaged, so the same problem as described above occurs.

Also, the configurations of placement positions of the switches of the conventional devices for holding surgery equipment do not take into consideration the axial direction of insertion of the endoscope. In other words, the configuration has been such that the relative position thereof changes according to the placement of the arm.

Accordingly, the surgeon cannot instantaneously know the direction which the endoscope is facing. Accordingly, there has been a problem in that it takes time to move the endoscope in the intended direction.

Also, equipment used for brain surgery and the like generally has a form wherein the surgeon pinches the equipment between his/her thumb and index finger. However, with conventional devices for holding surgery equipment, the grasping direction and insertion operating direction have differed with such equipment. In addition, unlike such equipment, the switches are in one location, so the surgeon tends not to be at ease with operating the surgery equipment holding device.

SUMMARY OF THE INVENTION

Accordingly, it is an object of the present invention to provide a surgery equipment holding device wherein, at the time of operating switches to disengage the fixed state, a sudden load is prevented from being placed on the hand of the surgeon holding the surgical equipment or on the surgical equipment being held in the surgeon's hand.

It is another object of the present invention to provide a surgery equipment holding device with excellent operability.

To this end, a surgery equipment holding device according to the present invention comprises: a holder for holding surgical equipment; a bar connected to the holder; a brake which operatively engages the bar for stopping movement of the bar; and a switch for switching being an active state and an inactive state of the brake.

The above and other objects, features and advantages of the invention will become more clearly understood from the following description referring to the accompanying drawings.

BRIEF DESCRIPTION OF THE DRAWINGS

FIGS. 1 through 5 relate to a first embodiment of the present invention, wherein:

FIG. 1 is a diagram illustrating a schematic configuration of a surgery equipment holding device;

FIG. 2 is a diagram illustrating the state of the surgery equipment holding device holding a therapeutic device in the equipment holding portion thereof;

FIG. 3 is a diagram explaining the structure of a fluid brake;

FIG. 4B is a diagram explaining the configuration of the fluid control unit provided with a variable diaphragm;

FIG. 5 is a block diagram explaining the primary configuration of the surgery equipment holding device;

FIGS. 8 and 9 relate to a third embodiment of the present invention, wherein:

FIG. 8 is a diagram explaining another configuration of the surgery equipment holding device;

FIG. 9 is a block diagram explaining the configuration of the surgery equipment holding device;

FIGS. 10 through 12B relate to a fourth embodiment of the present invention, wherein:

FIG. 10 is a diagram explaining yet another configuration of the surgery equipment holding device;

FIG. 11 is a cross-sectional diagram explaining the configuration of the grasping portion;

FIG. 12B is a block diagram explaining yet another configuration of the surgery equipment holding device;

FIGS. 13 through 14B relate to a fifth embodiment of the present invention, wherein:

FIG. 13 is a diagram explaining the principal configuration of the surgery equipment holding device;

FIG. 14B is a diagram explaining the position where the control circuit is disposed; and FIG. 15 is a diagram explaining a modification of the fifth embodiment.

DESCRIPTION OF THE PREFERRED EMBODIMENTS

A first embodiment of the present invention will now be described with reference to FIGS. 1 through 5.

Figure 1:
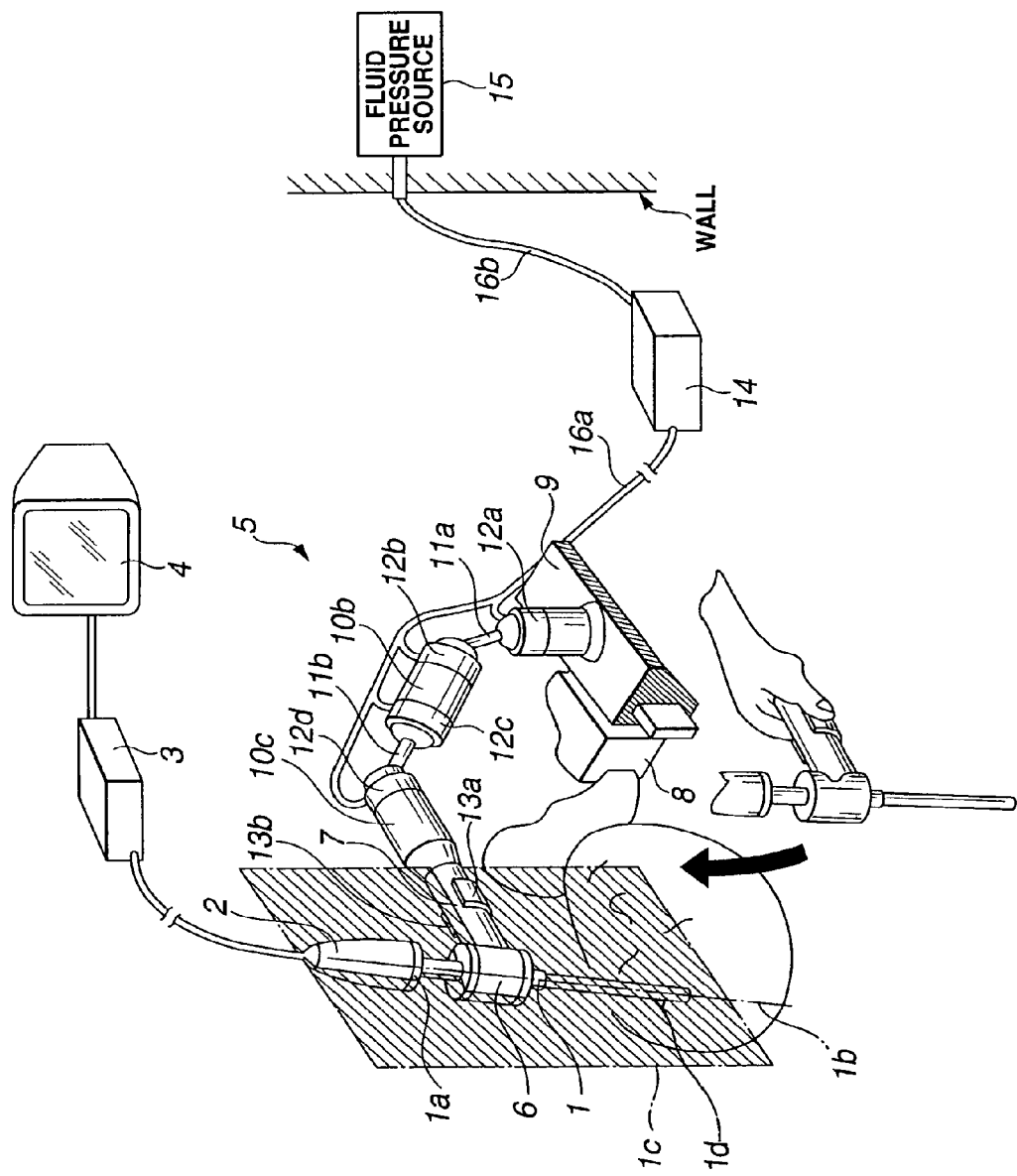

As shown in FIG. 1, a surgery equipment holding device according to the present invention has, for example, an endoscope 1 as a device for observing the part of the body which is the object of the surgery. A television camera head 2 having a CCD for example for picking up optical images of observed parts is mounted on an eyepiece 1a of the endoscope 1 having an insertion portion 1d capable of intracavital insertion. Images signals of the optical images converted by the unshown CCD provided to the television camera head 2 are generated as video signals at a controller 3 which is a video signals processing device. The video signals generated at the controller 3 are output to a monitor 4. Thus, endoscope images of the part observed are displayed on the screen of the monitor 4.

The endoscope 1 is held by a holding arm 5 serving as change holding means. The holding arm 5 is of a configuration which allows the position and direction of the endoscope 1 being held to be changed.

Disposed on the tip side of the holding arm 5 which is one edge thereof are an equipment holding portion 6 for holding the endoscope 1, and a grasping portion 7 for the surgeon to grasp. On the other hand, an attaching portion 9 is provided to the other end of the holding arm 5, for being fixed to a surgery table 8, for example.

Figure 2:
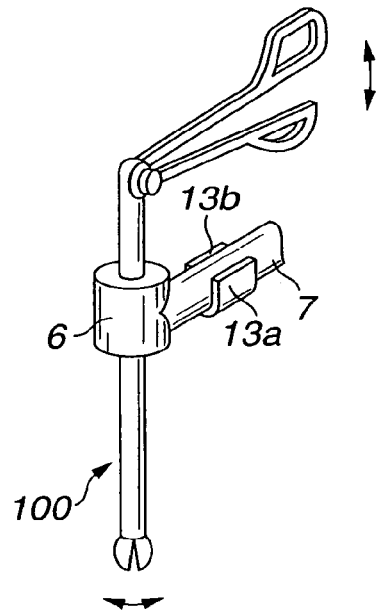

While the present embodiment is described with the endoscope 1 as an example of the surgery equipment held by the equipment holding portion 6, therapeutic devices such as forceps 100, a type of surgical equipment, may be held by the equipment holding portion 6, as shown in FIG. 2.

The holding arm 5 has a first arm 10a, a second arm 10b, and a third arm 10c, serially linked from the attaching portion 9 side. A first rod 11a and a second rod 11b are disposed between the first arm 10a and the second arm 10b, and between the second arm 10b and the third arm 10c, respectively.

A first fluid brake 12a, a second fluid brake 12b, a third fluid brake 12c, and a fourth fluid brake 12d, serving as fixation maintaining means are disposed at the joint portions between the first arm 10a and first rod 11a, second arm 10b and the first rod 11a, the second arm 10b and second rod 11b, and third arm 10c and the second rod 11b, respectively.

A first switch 13a and second switch 13b are provided as a pair, as fixation disengaging instructing means, to the grasping portion 7. The first switch 13a and the second switch 13b are disposed so as to be in planar symmetrical positional relation across a plane 1c, the hatched portion in the figure, which contains the insertion axis 1b of the endoscope 1.

The first switch 13a and second switch 13b are electrically connected to a fluid control unit 14 which is a fixation force control means. A first fluid hose 16a and second fluid hose 16b, which are channels for a pressured fluid, extend from the fluid control unit 14.

The end of the second fluid hose 16b is coupled to a fluid pressure source 15 for supplying compressed air or compressed nitrogen gas, commonplace in surgery rooms. On the other hand, the end of the first fluid hose 16a branches into several parts at the base end side. The branched ends each couple with the first fluid brake 12a, second fluid brake 12b, third fluid brake 12c, and fourth fluid brake 12d.

The first switch 13a and second switch 13b are known push-button switches for example, and are contact switches having contacts. The first switch 13a and second switch 13b are electrically serially connected to a later-described control circuit 35 provided within the fluid control unit 14.

Now, the structure of the first fluid brake 12a will be described with reference to FIG. 3.

Note that the structure of the second fluid brake 12b, third fluid brake 12c, and fourth fluid brake 12d, are the same as that of the first fluid brake 12a. Accordingly, the structure of the first fluid brake 12a alone will be described, and that of the second fluid brake 12b, third fluid brake 12c, and fourth fluid brake 12d will be omitted.

As shown in the figure, the first arm 10a of the first fluid brake 12a has a hollow structure. Disposed within the first arm 10a are a generally-spherically formed ball end 21 formed on the end of the rod 11a with a radius R, and a pressing portion 20 of a predetermined form.

An abutting portion 17, formed of the spherical face having a radius R, is provided at the tip of the inside of the first arm 10a. Accordingly, the ball end 21 comes into planar contact with this abutting portion 17. Note that the point A in the figure represent the center of the abutting portion 17 and the ball end 21.

The pressing portion 20 comprises a pressing member 22, a shaft 23, and a piston 24. The pressing member 22 has a pressing face for pressing the ball end 21. The shaft 23 is integrally provided on the base face of the pressing member 22. The piston 24 is integrally provided on the base face of the shaft 23.

A protrusion 18 is formed in the inside of the first arm 10a. A spring 25 is disposed between this protrusion 18 and the pressing member 22, in a compressed state. Accordingly, the pressing force of the spring 25 acts to press the pressing member 22. Consequently, the pressing member 22 pressing the ball end 21 causes the ball end 21 and the abutting portion 17 to be pressed one against another, so as to be in a fixed and held state.

Figure 3:
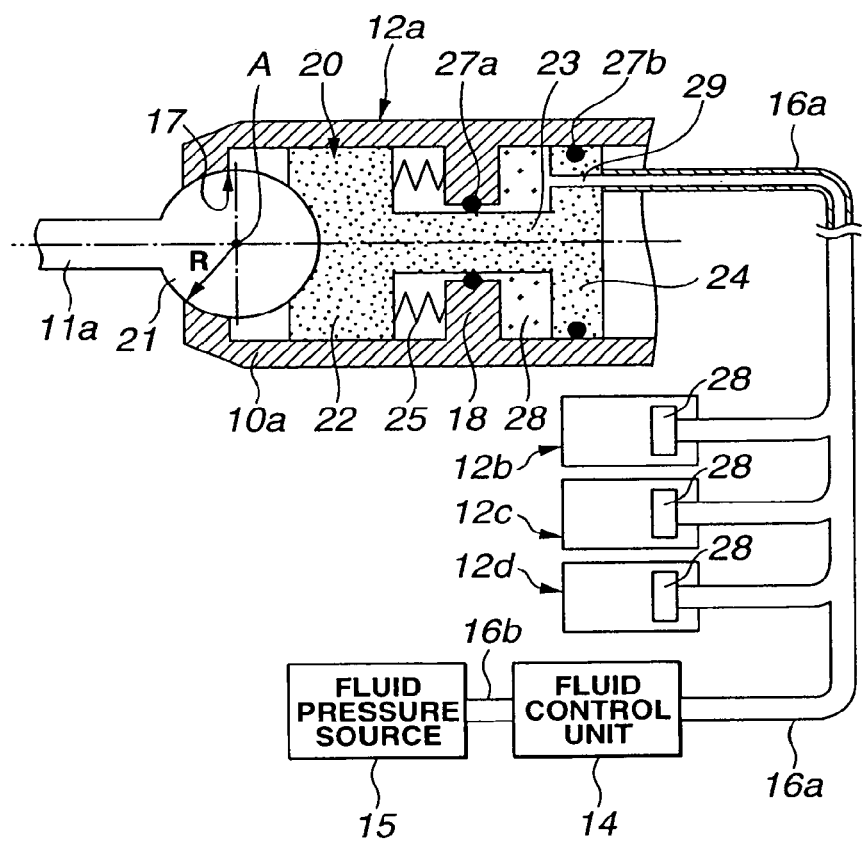

As shown in FIG. 3, a first o-ring 27a for maintaining an airtight state is disposed between the protrusion 18 and the shaft 23. Also, a second o-ring 27b for maintaining an airtight state is disposed between the inner circumference of the piston 24 and the first arm 10a. Providing these o-rings 27a and 27b makes the space defined by the first arm 10a and shaft 23 and piston 24 to be an airtight space 28. An inlet port 29 communicating with the airtight space 28 is formed in the piston 24. The end of the hose 16a is communicably connected to this inlet port 29.

The structure of the fluid control unit 14 will be described with reference to FIGS. 4A and 5.

As shown in these figures, an electromagnetic valve 30, serving as known means for switching channels, is disposed in the fluid control unit 14. The electromagnetic valve 30 has three ports 31a, 31b, and 31c, serving as the input channel, discharge channel, and functioning channel, for the pressured fluid. A known solenoid 32 configured of a coil 33 and shaft 34 are provided to the electromagnetic valve 30. The coil 33 of the solenoid 32 is electrically connected to the first switch 13a and second switch 13b via the control circuit 35.

A valve 36 is integrally provided on the tip side of the shaft 34. In the event that this valve 36 is at the position indicated by solid lines in the figure, the port 31b and the port 31a are in a communicating state. On the other hand, in the event that the valve 36 is at the position indicated by dotted lines in the figure, the port 31b and the port 31c are in a communicating state. That is to say, the configuration is such that the channels are switched by the valve 36 moving.

A spring 37 is disposed between the shaft 34 and a housing 38. The valve 36 is placed at the position indicated by the solid lines due to the pressing force of this spring 37.

A known diaphragm 39, capable of narrowing down the cross-sectional area of the fluid tube, is disposed between the port 31c of the electromagnetic valve 30 and an inlet port 40. The inlet port 40 is coupled to a fluid pressure source 15 via a hose 16b, such that the connection is airtight, while allowing the fluid to pass through.

The hose 16a is coupled to the port 31b. The base portion of the hose 16a is connected to the inlet port 40 communicating with the airtight space 28 formed at each of the first fluid brake 12a, second fluid brake 12b, third fluid brake 12c, and fourth fluid brake 12d, such that the connection is airtight, while allowing the fluid to pass through.

The port 31a is opened to the atmosphere via an vent tube 41.

The cross-sectional area Qx (m$^2$) of the fluid channel of the diaphragm 39 and the cross-sectional area Qy (m$^2$) of the vent tube 41 are set in a relation such that $$Qx \ll Qy$$

holds.

Now, the operation of the surgery equipment holding device configured thus will be described.

First, the fixation holding state of the surgery equipment holding device will be described.

At the time of this fixation holding state, the first switch 13a and the second switch 13b are unpressed, and the valve 36 is situated at the position indicated by the solid line in the figure by the pressing force of the spring 37. Accordingly, the port 31b and the port 31a are in a communicating state.

Thus, the vent tube 41 and the airtight space 28 are communicating via the port 31a, port 31b, and hose 16a. In other words, the airtight space 28 is released to the atmosphere.

Consequently, the pressing portions 20 within the first fluid brake 12a, second fluid brake 12b, third fluid brake 12c, and fourth fluid brake 12d are pressed against the abutting portion 17 side by the pressing force of the spring 25. As a result, the ball end 21 is pressed and fixed against the abutting portion 17 by a fixing force of F (N), by the pressing member 22 making up the pressing portion 20.

That is to say, the endoscope 1 is fixed and held in a constant position, due to the rod 11a and the rod 11b being in a fixed state.

Now, in this fixation state, the pressured fluid in the fluid pressure source 15 is in a pressured and filled state near to around the port 31c, via the hose 16b, inlet port 40, and diaphragm 39.

Next, the operation for causing the fixed and held endoscope 1 to move will be described.

In the event of moving the endoscope 1, the fixation holding state of the first fluid brake 12a, second fluid brake 12b, third fluid brake 12c, and fourth fluid brake 12d is disengaged. To this end, the surgeon presses and operates the first switch 13a and the second switch 13b disposed on the grasping portion 7.

Note that the relative positional relation between the first switch 13a and the second switch 13b disposed on the grasping portion 7 and the endoscope 1 is always the same, regardless of the attitude of the holding arm 5.

Also, as described above, the first switch 13a and the second switch 13b are disposed so as to be in plane symmetrical positional relation across a plane 1c which contains the insertion axis 1b of the endoscope 1. Accordingly, the surgeon can operate while grasping the grasping portion 7 and pinching the first switch 13a and the second switch 13b with the thumb and index finger.

The surgeon simultaneously pressing and operating the first switch 13a and the second switch 13b brings the electromagnetic valve 30 to action. The action of the electromagnetic valve 30 causes the valve 36 to move against the pressing force of the spring 37 due to a solenoid 32 from the position indicated by solid lines to the position indicated by dotted lines. Thus, the port 31b and the port 31c are in a communicating state. This causes the pressured fluid which had been filled in a pressurized state up to the port 31c to flow into the airtight space 28 via the port 31b and the hose 16a. That is to say, the pressured fluid continues to pass through the diaphragm 39 formed with a cross-sectional area Qx (m$^2$) into the airtight space 28, until an isopiestic state is attained between the airtight space 28 and the fluid pressure source 15.

Once the pressure within the airtight space 28 begins to rise, reaction force is generated at the piston 24 against the pressing force of the spring 25 pressing the pressing member 22. That is, the pressing force pressing the ball end 21 of the pressing portion 20 gradually drops. Finally, the pressed fixation state of the ball end 21 which had been pressed and fixed against the abutting portion 17 by the pressing portion 20, is disengaged.

This allows the ball ends 21 disposed within the first fluid brake 12a, second fluid brake 12b, third fluid brake 12c, and fourth fluid brake 12d to rotate on the center point A. That is to say, the first rod 11a and the second rod 11b become movable. Thus, the surgeon can move the endoscope 1 to a desired position.

Next, description will be made regarding a case wherein the surgeon fixes the endoscope 1 again.

Upon moving the endoscope 1 to the desired position, the surgeon releases his/her fingers from the first switch 13a and the second switch 13b to fix and hold the position of the endoscope 1. This causes the valve 36 of the electromagnetic valve 30 to return from the position indicated by dotted lines to the position indicated by solid lines, due to the pressing force of the spring 37. Thus, the port 31a and the port 31b communicate.

At this time, the pressured fluid filling the airtight space 28 immediately is released into the atmosphere through the vent tube 41 formed with a cross-sectional area Qy ($m^2$), via the ports 31b and 31a. Consequently, the reaction force decreases, the pressing portion 20 is pressed by the pressing force of the spring 25, and the ball end 21 is pressed and fixed against the abutting portion 17. Thus, the endoscope 1 is in a fixed and held state at the position to which the surgeon has moved it.

That is to say, at the time of disengaging the fixation, the pressured fluid passes through the diaphragm 39 formed with a cross-sectional area Qx ($m^2$). Conversely, at the time of fixing, the pressured fluid passes through the vent tube 41 formed with a cross-sectional area Qy ($m^2$).

Now, the relation of Qx<<Qy has been set between Qx and Qy, so the amount of fluid passing through these channels per unit time is in the same relation as with the relation of cross-sectional area. That is, the difference set here in the amount of fluid passing through causes the disengaging action of the surgery equipment holding device to be carried out gradually. On the other hand, the fixing action of the surgery equipment holding device is performed rapidly. Accordingly, there is no sudden placing of a load on the hand of the surgeon at the time of disengaging the fixation, while the endoscope is speedily fixed at the time of fixation.

In this way, the cross-sectional area of the channels through which the pressured fluid passes at the time of disengaging fixation and at the time of fixing is set such that the cross-sectional area of the channel through which the pressured fluid passes at the time of disengaging fixation is smaller than the cross-sectional area of the channel through which the pressured fluid passes at the time of fixing, so that on one hand, while the surgeon can disengage the fixed state of the endoscope without any sudden placing of holding load on the hand of the surgeon, on the other hand, the endoscope can be speedily set in a fixed state at the time of fixing.

Thus, at the time of moving the surgery equipment, the surgeon can smoothly move the surgery equipment to the desired position without losing sight of the part of the body to be observed or treated. Accordingly, the working time can be reduced, the fatigue of the surgeon can be lightened, and surgery efficiency improves greatly.

Also, control of fixation disengagement and fixing can be performed using the pressured fluid of a fluid pressure source normally installed in surgery rooms, so there is no need to prepare a new fluid pressure source or install complicated control circuits, and accordingly ease-of-use is facilitated.

Further, a small and simple structure can be realized, by adopting simple electrical contact switches as the switches. In addition, by electrically connecting a pair of switches serially to the control circuit instruction signals can be surely prevented from being output in the event that only one switch is operated.

Also, the relative positional relation between the switches and the plane containing the axis of the endoscope is constant, thereby solving the problem of the surgeon having to confirm the position each time when moving the surgery equipment held by the surgery equipment holding device to a desired position and fixing the surgery equipment thereat, so time efficiency in the surgery can be achieved as well.

Note that in the present embodiment, the fluid pressure source 15 is described as a configuration using compressed air or compressed nitrogen gas or the like installed in the surgery room, but the pressured fluid is not restricted to these, and oil, viscous fluids, etc., capable of being compressed, may be used.

Also, with the present embodiment, the configuration indicated uses an electromagnetic valve 30 for switching channels, but the switching of the channels is not restricted to an electromagnetic valve; rather, any channel switching means capable of switching channels according to instructions from the first switch 13a and second switch 13b is sufficient, and another example will be described later.

Next, a modification of the first embodiment will be described with reference to FIG. 4B.

Figure 4A:
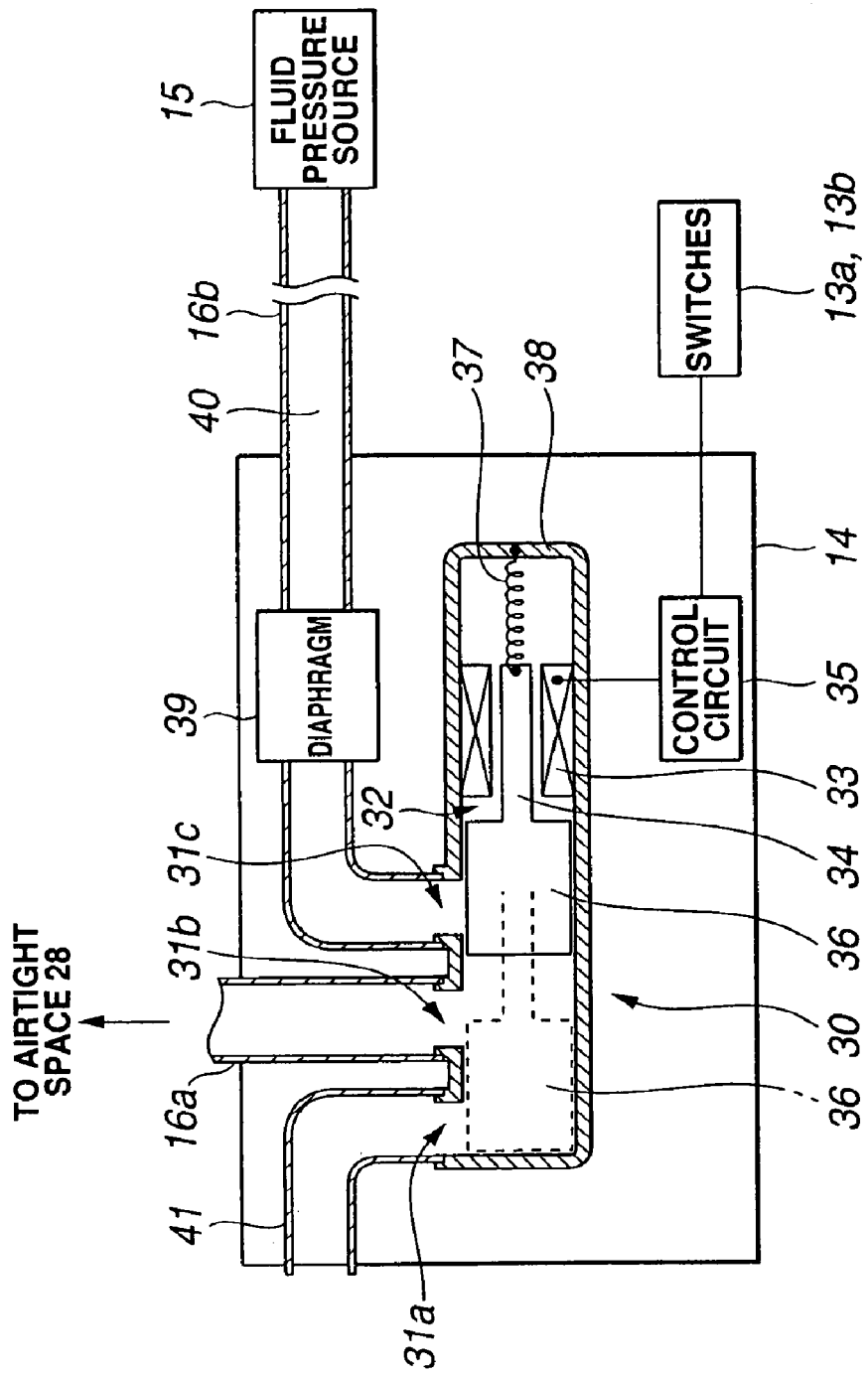
FIG. 4A is a diagram explaining the structure of a fluid control unit.
Figure 5:
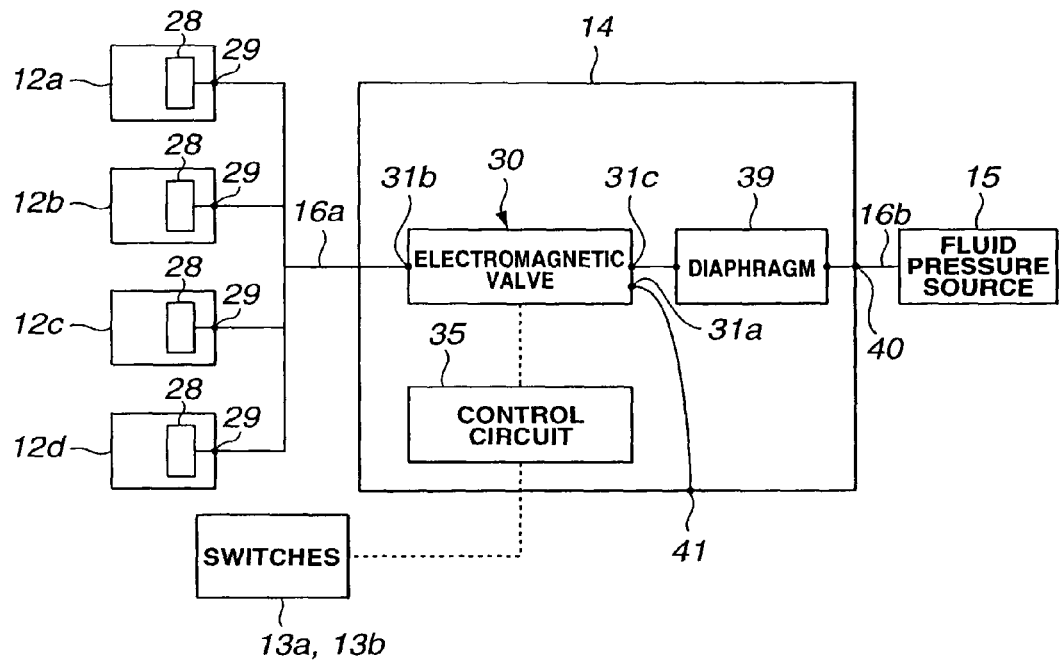

As shown in the figure, with the present embodiment, the diaphragm 39 provided to the inlet port 40 in FIG. 4A has been changed to a variable diaphragm 39a. The variable diaphragm 39a allows the operator to set the fluid influx to a desired amount. That is to say, this variable diaphragm 39a allows the amount of influx of the fluid to the airtight space 28 to be suitably adjusted in increments of time. Consequently, the surgeon can set the time which elapses till the brakes are disengaged to a desired value, and can smoothly move the surgery equipment to the object part. Thus, according to the present embodiment, the operability of the device improves, and fatigue of the surgeon is alleviated.

Further, in FIG. 4B, a variable diaphragm 39b is provided to the vent tube 41 as well, so that the operator can set the amount of fluid discharged to a desired amount. That is to say, this variable diaphragm 39b allows the amount of fluid discharged from the airtight space 28 to be suitably adjusted in increments of time. Consequently, the surgeon can set the time which elapses till the brakes are active, to a desired value.

Now, it is generally held to be true that the time required for the brakes to become active should be as short as possible. However, it is also undeniable that there are timings which are intuitively acceptable and unacceptable according to individuals. In regard to this, the present embodiment allows the time for the fluid to flow into the airtight space 28 via the variable diaphragm 39a to be adjusted, and the variable diaphragm 39b can be adjusted to achieve matching with the capacity of the airtight space 28 itself, so a surgery equipment holding device capable of reducing fatigue, which is suitably operable and meets the preferences of each of multiple surgeons, can be provided.

Note that in the event that the only object of the surgeon is to smoothly move the surgery equipment to the object part, all that is necessary is to set the time until the brakes are disengaged. In other words, the object of the present embodiment can be achieved simply by adding the variable diaphragm 39a in order to adjust the timing of disengaging the brakes to the preference of the surgeon.

Figure 6:
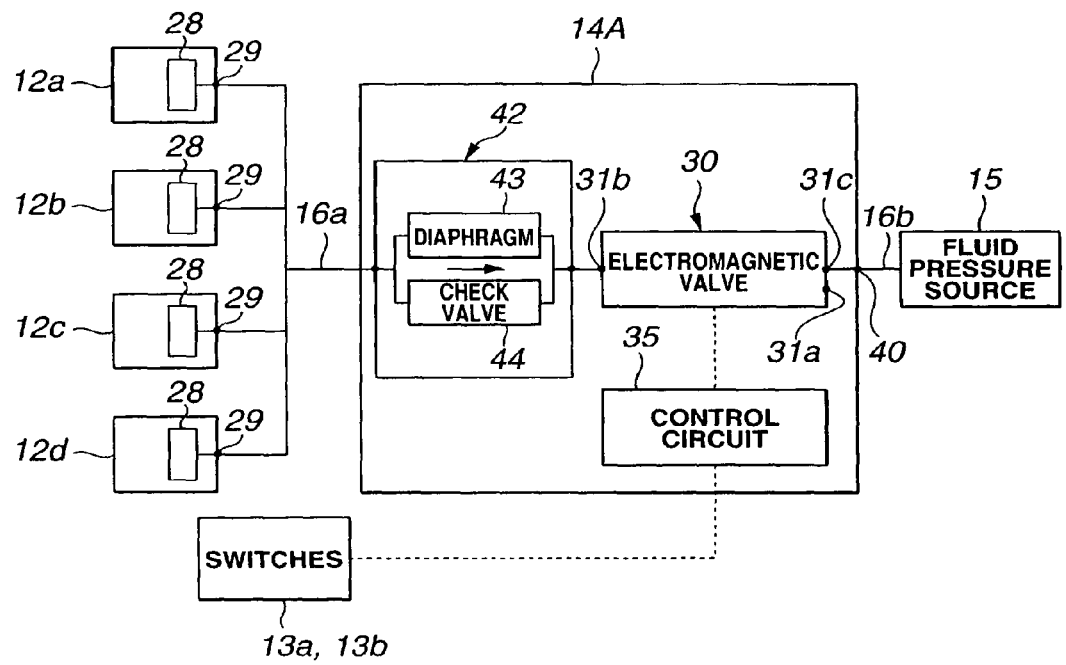
FIG. 6 is a block diagram explaining the configuration of the surgery equipment holding device according to a modification of the first embodiment.

Next, a modification of the first embodiment will be described with reference to FIG. 6.

As shown in the figure, with the present embodiment, the configuration of the fluid control unit 14 serving as the fixing force control means has been changed as follows.

With the fluid control unit 14A according to the present embodiment, a directional diaphragm unit 42 is disposed between the port 31b of the electromagnetic valve 30 and the hose 16a. This directional diaphragm unit 42 comprises a diaphragm 43 and a check valve 44 which allows the fluid to only flow in the one direction indicated by the arrow.

That is, the check valve 44 is provided such that only the fluid from the airtight spaces 28 formed in the first fluid brake 12a, second fluid brake 12b, third fluid brake 12c, and fourth fluid brake 12d, passes.

Also, the cross-sectional area Qx1 of the diaphragm 43 and the cross-sectional area Qy1 of the check valve 44 are set in a relation such that $$Qx1 \ll Qy1$$

holds. That is to say, the relation is set such that the cross-sectional area of the channel through which the pressured fluid passes at the time of disengaging fixation is smaller than the cross-sectional area of the channel through which the pressured fluid passes at the time of fixing.

The surgeon simultaneously pressing and operating the first switch 13a and the second switch 13b in order to disengage the fixed state of the endoscope 1 brings the electromagnetic valve 30 to action, and the port 31b and the port 31c communicate. This causes the pressured fluid to pass through the port 31c and port 31b and then flow into the directional diaphragm unit 42. The pressured fluid which flows into the directional diaphragm unit 42 then passes through the diaphragm 48 and enters the airtight space 28 to act in the same manner as with the first embodiment.

On the other hand, upon the surgeon releasing his/her fingers from the first switch 13a and the second switch 13b to fix and hold the position of the endoscope 1, the pressured fluid filling the airtight space 28 immediately is released into the atmosphere, as with the first embodiment, primarily through the check valve 44.

That is to say, at the time of flowing into the airtight space 28, the pressured fluid passes through the diaphragm 43 formed with a cross-sectional area Qx1. On the other hand, at the time of flowing out of the airtight space 28, the pressured fluid passes through the check valve 44 formed with a cross-sectional area Qy1.

Now, the relation of Qx1<<Qy1 has been set between Qx1 and Qy1, so as with the first embodiment, causes the disengaging action of the surgery equipment holding device to be carried out gradually, and the fixing action of the surgery equipment holding device to be performed rapidly. That is to say, operations and advantages similar to those of the first embodiment can be obtained at the time of disengaging the fixation and at the time of fixing.

In this way, a simple configuration that is easy to use can be realized by using a known diaphragm and check valve in the directional diaphragm unit.

Figure 7:
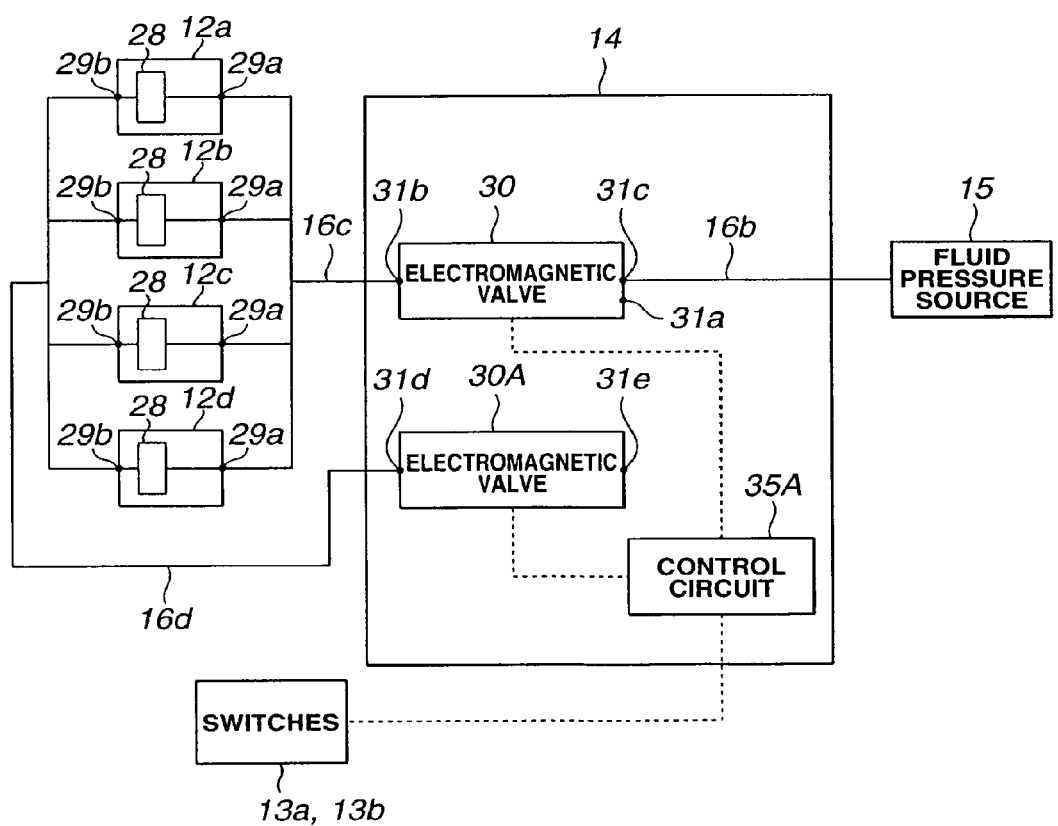
FIG. 7 is a block diagram explaining another configuration of the surgery equipment holding device according to a second embodiment of the present invention.

A second embodiment of the present invention will be described with reference to FIG. 7.

Note that with the present embodiment, components common to the first embodiment will be denoted with the same reference numerals and description thereof will be omitted.

As shown in the figure, the fluid pressure source 15 according to the present embodiment is coupled to the port 31c of the electromagnetic valve 30 via the hose 16b. The port 31b of the electromagnetic valve 30, and an inlet port 29a communicating with the airtight spaces 28 formed at each of the first fluid brake 12a, second fluid brake 12b, third fluid brake 12c, and fourth fluid brake 12d, are coupled by an inlet hose 16c. The fluid channel of the port 31a of the electromagnetic valve 30 according to the present embodiment is closed off.

On the other hand, a discharge port 29b, which is a fluid channel, is provided at the airtight spaces 28 communicating with the inlet ports 29a of the first fluid brake 12a, second fluid brake 12b, third fluid brake 12c, and fourth fluid brake 12d.

One end of a vent hose 16d making up the fluid channel is coupled to the discharge port 29b. The other end of the vent hose 16d is coupled to a port 31d of an electromagnetic valve 30A having a configuration generally the same as that of the electromagnetic valve 30.

Now, the relation is set such that the cross-sectional area Qx2 of the inlet hose 16c is smaller than the cross-sectional area Qy2 of the vent hose 16d.

The electromagnetic valve 30A has, in addition to the port 31d, a port 31e released to the atmosphere. The port 31d and port 31e of the electromagnetic valve 30A are of a configuration controllable by a control circuit 35A.

The first switch 13a and the second switch 13b are electrically connected to the control circuit 35A. The control circuit 35A is electrically connected to each of the electromagnetic valve 30 and the electromagnetic valve 30A. In the present embodiment, the control circuit 35A, the electromagnetic valve 30 and the electromagnetic valve 30A, and the inlet hose 16c and the vent hose 16d make up the fixing force control means.

Now, the operation of the surgery equipment holding device configured thus will be described.

First, the surgeon presses and operates the first switch 13a and the second switch 13b. As a result, at the control circuit 35A, the port 31c and port 31b provided on the electromagnetic valve 30 are in a communicating state, while the channel to the port 31d of the electromagnetic valve 30A is closed off. Accordingly, the pressured fluid supplied from the fluid pressure source 15 passes through the hose 16b, electromagnetic valve 30, and inlet hose 16c, and flows into the airtight space 28, thereby raising the internal pressure. Consequently, as with the first embodiment, the fixing force of the first fluid brake 12a, second fluid brake 12b, third fluid brake 12c, and fourth fluid brake 12d drop, attaining a fixation disengagement state.

Next, when the surgeon releases the first switch 13a and the second switch 13b, at the control circuit 35A, the port 31a and port 31b of the electromagnetic valve 30 are in a communicating state, while the port 31d and port 31e of the electromagnetic valve 30A are also in a communicating state. At this time, the fluid channel to the port 31c is closed off.

Accordingly, the pressured fluid filling the airtight space 28 is released into the atmosphere via the vent hose 16d, port 31d, and port 31e. Consequently, as with the first embodiment, the first fluid brake 12a, second fluid brake 12b, third fluid brake 12c, and fourth fluid brake 12d are in a fixed state.

Now, the cross-sectional area of the inlet hose 16c is set to be smaller than the cross-sectional area of the vent hose 16d, so the amount of change in pressure of the airtight space 28 per time increment is smaller at the time of disengaging the fluid brake fixation. Consequently, operations and advantages the same as those of the first embodiment can be obtained.

In addition, with the present embodiment, a common fluid channel for pressured fluid to pass through at the fixation action time and the fixation disengagement action time is not configured. Accordingly, the channel for pressured fluid at the fixation action time and the channel for pressured fluid at the fixation disengagement action time are independently configured. Accordingly, action control for each can be independently designed and disposed, thereby realizing handy and easy high-precision control.

While the present embodiment is described with a configuration using an inlet hose 16*c*, other configurations may be used, such as one with a diaphragm disposed instead of the inlet hose 16*c*.

A third embodiment of the present invention will be described with reference to FIGS. 8 and 9.

Note that with the present embodiment, components common to the above-described embodiments will be denoted with the same reference numerals and description thereof will be omitted.

Figure 8:
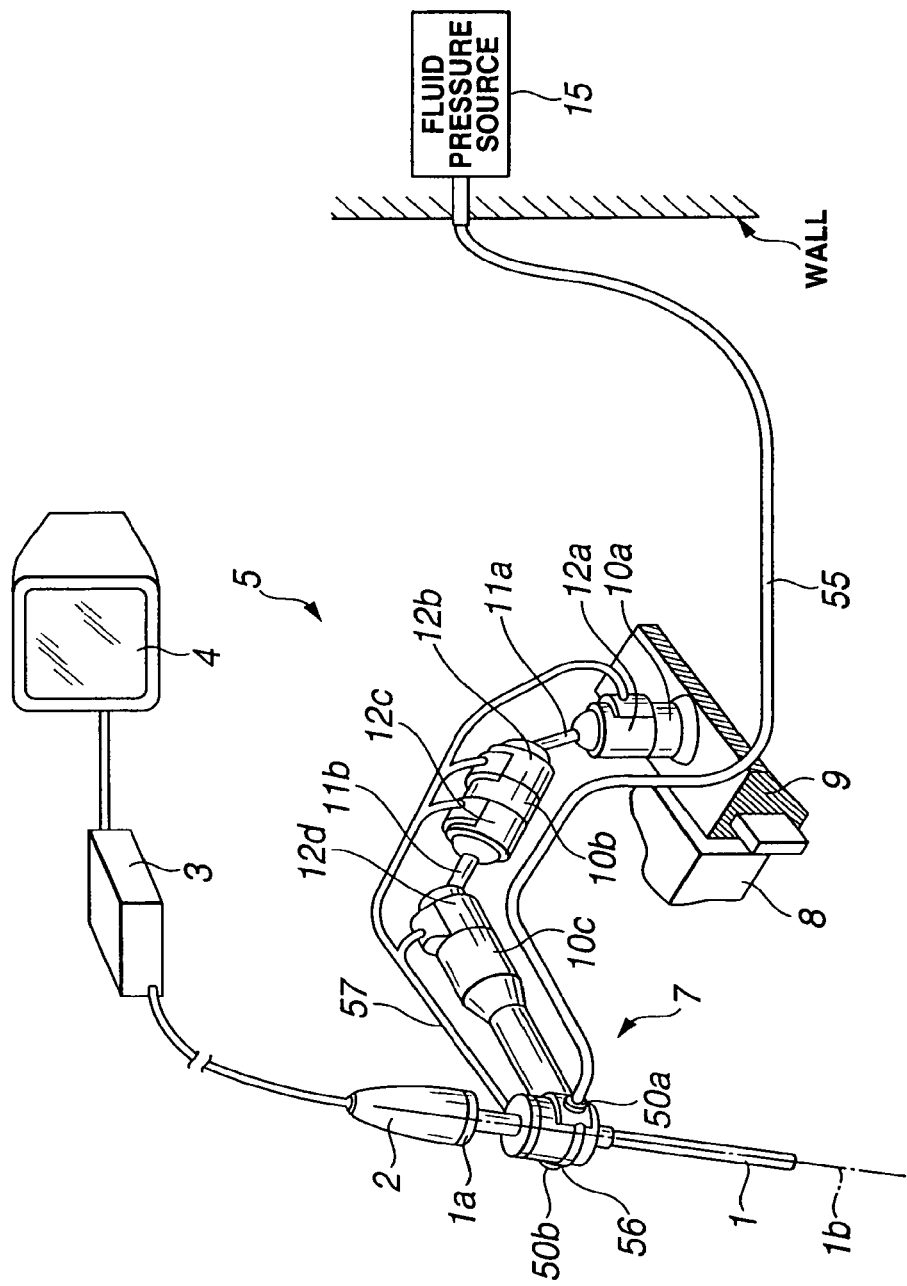

As shown in FIG. 8, with the present embodiment, mechanical switches denoted by reference numerals 50*a* and 50*b* are provided at the equipment holding portion 6. The mechanical switches 50*a* and 50*b* are fixation disengaging instructing means capable of mechanically controlling the pressured fluid which is the acting energy of the first fluid brake 12*a*, second fluid brake 12*b*, third fluid brake 12*c*, and fourth fluid brake 12*d*, which are fixation maintaining means. The mechanical switches 50*a* and 50*b* are disposed at axially symmetrical positions as to the insertion axis 1*b* of the endoscope 1.

Figure 9:
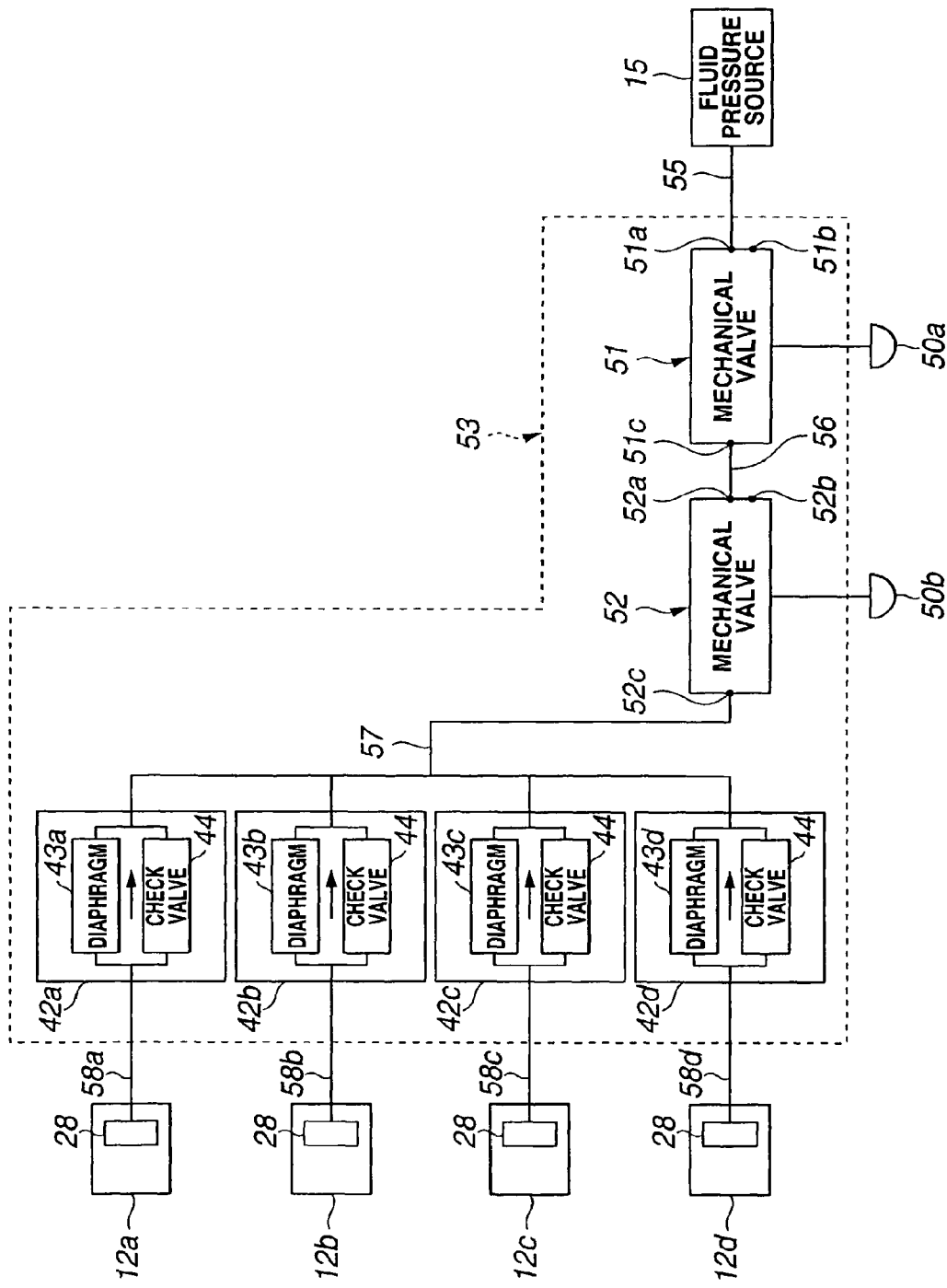

As shown in FIG. 9, known mechanical valves, denoted by reference numerals 51 and 52, are provided at the mechanical switches 50*a* and 50*b*. These mechanical valves 51 and 52 are respectively joined to the mechanical switches 50*a* and 50*b* which are manual push-button switches integrally joined to the axis 34 instead of the electromagnetic valve 30 shown in FIG. 4A according to the first embodiment.

As with the electromagnetic valve 30 in the first embodiment, the mechanical valves 51 and 52 have respective input ports 51*a* and 52*a*, discharge ports 51*b* and 52*b*, and functioning ports 51*c* and 52*c*.

Now, the operation of the mechanical valve 51 will be described. Note that the action of the mechanical valve 52 is the same as the action of the mechanical valve 51. Accordingly, only the mechanical valve 51 will be described here, and description of the mechanical valve 52 will be omitted.

The mechanical valve 51 is channel switching means, and normally, in the state that the mechanical switch 50*a* is not pressed, the discharge port 51*b* and the functioning port 51*c* are in a communicating state. When the mechanical switch 50*a* is in a pressed state, the input port 51*a* and the functioning port 51*c* are in a communicating state.

A hose 55 extending from the fluid pressure source 15 is coupled to the input port 51*a* of the mechanical valve 51, such that the connection is airtight, while allowing the fluid to pass through. The functioning port 51*c* of the mechanical valve 51 and the input port 52*a* of the mechanical valve 52 are coupled via a hose 56, such that the connection is airtight, while allowing the fluid to pass through.

Further, a hose 57 is coupled to the functioning port 52*c* of the mechanical valve 52, and each of the branched ends of the hose 57 are connected to one end of directional diaphragm units 42*a*, 42*b*, 42*c*, and 42*d*, each having a configuration that same as the directional diaphragm unit 42 described in the first embodiment.

The other end of the directional diaphragm units 42*a*, 42*b*, 42*c*, and 42*d*, and the airtight space 28 of the first fluid brake 12*a*, second fluid brake 12*b*, third fluid brake 12*c*, and fourth fluid brake 12*d*, respectively communicate via hoses 58*a*, 58*b*, 58*c*, and 58*d*.

Note that both discharge ports 51*b* and 52*b* are opened to the atmosphere.

Also, the check valves 44 provided within the directional diaphragm units 42*a*, 42*b*, 42*c*, and 42*d* are disposed so that the pressured fluid within the airtight spaces 28 will pass.

Further, the diameter dimensions of diaphragms 43*a*, 43*b*, 43*c*, and 43*d*, disposed within the directional diaphragm units 42*a*, 42*b*, 42*c*, and 42*d*, are set such that the relation $\Phi a < \Phi b < \Phi c < \Phi d$ holds.

With the present embodiment, the directional diaphragm units 42*a*, 42*b*, 42*c*, and 42*d*, and the mechanical valves 51 and 52 make up the fluid control unit 53 serving as the fixation force control means.

The operation of the surgery equipment holding device configured as described above will now be described.

First, description will be made regarding a case of the surgeon moving the endoscope 1.

In the event that the surgeon operates the mechanical switch 50*a*, the input port 51*a* and the functioning port 51*c* are placed in a communicating state at the mechanical valve 51. Also, in the event that the surgeon operates the mechanical switch 50*b*, the input port 52*a* and the functioning port 52*c* are placed in a communicating state at the mechanical valve 52.

In the event that the surgeon operates both the mechanical switch 50*a* and the mechanical switch 50*b* simultaneously, the pressured fluid from the fluid pressure source 15 passes through the hose 55, input port 51*a*, functioning port 51*c*, hose 56, input port 52*a*, and functioning port 52*c*, in that order, and flows into the hose 57. The pressured fluid which has flowed into the hose 57 flows into the airtight space 28 of the first fluid brake 12*a*, second fluid brake 12*b*, third fluid brake 12*c*, and fourth fluid brake 12*d*, via the directional diaphragm units 42*a*, 42*b*, 42*c*, and 42*d* which are disposed in parallel on the hose 57.

Now, the relation of the moment Ma, Mb, Mc, and Md, as to the load necessary for holding the endoscope, with regard to the first fluid brake 12*a*, second fluid brake 12*b*, third fluid brake 12*c*, and fourth fluid brake 12*d*, is Ma>Mb>Mc>Md.

That is to say, the moment Md placed on the fulcrum A within the fourth fluid brake 12*d* is the load from the third arm 10*c* to the endoscope 1. In comparison, the moment Mc placed on the fulcrum A within the third fluid brake 12*c* is the load from the rod 11*b* to the endoscope 1. Also, the moment Mb placed on the fulcrum A within the second fluid brake 12*b* is the load from the second arm 10*b* to the endoscope 1, and the moment Ma placed on the fulcrum A within the first fluid brake 12*a* is the load from the rod 11*a* to the endoscope 1.

On the other hand, the relation $\Phi a < \Phi b < \Phi c < \Phi d$ holds for the diaphragms 43*a*, 43*b*, 43*c*, and 43*d*, with the channel cross-sectional areas being adjusted according to the moment Ma, Mb, Mc, and Md relating to the first fluid brake 12*a*, second fluid brake 12*b*, third fluid brake 12*c*, and fourth fluid brake 12*d*, so as to act such that the first fluid brake 12*a*, second fluid brake 12*b*, third fluid brake 12*c*, and fourth fluid brake 12*d* all are disengaged simultaneously and at the same speed.

Next, description will be made regarding a case of the surgeon fixing the endoscope 1.

When the surgeon releases the mechanical switches 50*a* and 50*b*, as with the first embodiment, the first fluid brake 12*a*, second fluid brake 12*b*, third fluid brake 12*c*, and fourth fluid brake 12*d* are immediately placed in a fixed state.

That is to say, the fixation disengaging action of the surgery equipment holding device is carried out gradually, while the fixing action of the surgery equipment holding device is performed rapidly. Thus, at the time of disengaging, the fixed state of the endoscope can be disengaged without applying a sudden holding load on the hand of the surgeon, while on the other hand, the endoscope 1 can be rapidly fixed at the time of fixing.

Thus, with the present embodiment, no electrical control is used whatsoever, so the configuration can be made even more simple.

Also, the fixation disengaging speed can be set to be different according to the difference of moment relating to the fluid brakes, so an even more operable surgery equipment holding device can be provided, by arranging the fixation of the joints to be disengaged at the same speed as to the holding hand of the surgeon.

Further, the mechanical switches are disposed axially symmetrical as to the insertion axis of the endoscope, resulting in a form where the surgeon grasps the endoscope itself. Accordingly, the surgeon can grasp the position on the endoscope even more easily than with the first embodiment.

Accordingly, the problem of fatigue on the surgeon, which is caused by difference in operability wherein the relative positional relation between the switches and the surgery equipment differs from one surgical therapeutic device to another, can be lessened.

A fourth embodiment of the present invention will be now described with reference to FIGS. 10 to 12B.

Note that with the present embodiment, components common to the above-described embodiments will be denoted with the same reference numerals and description thereof will be omitted.

Figure 10:
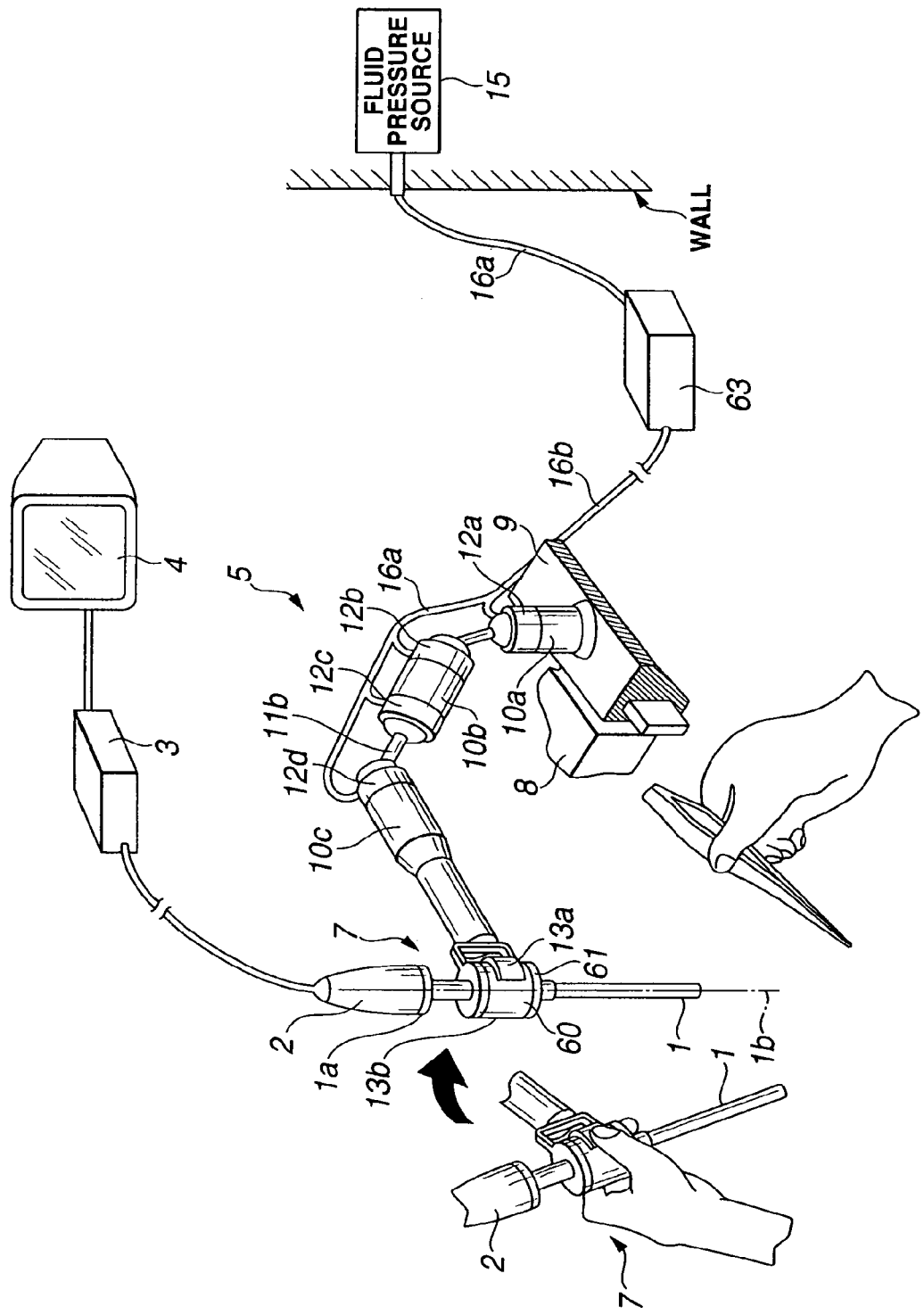

As shown in FIG. 10, the grasping portion 7 according to the present embodiment is configured of a holding member 61 and rotating member 60. The holding member 61 is connected and fixed to the third arm 10c. The rotating member 60 has a configuration rotatably attached to the holding member 61.

Figure 11:
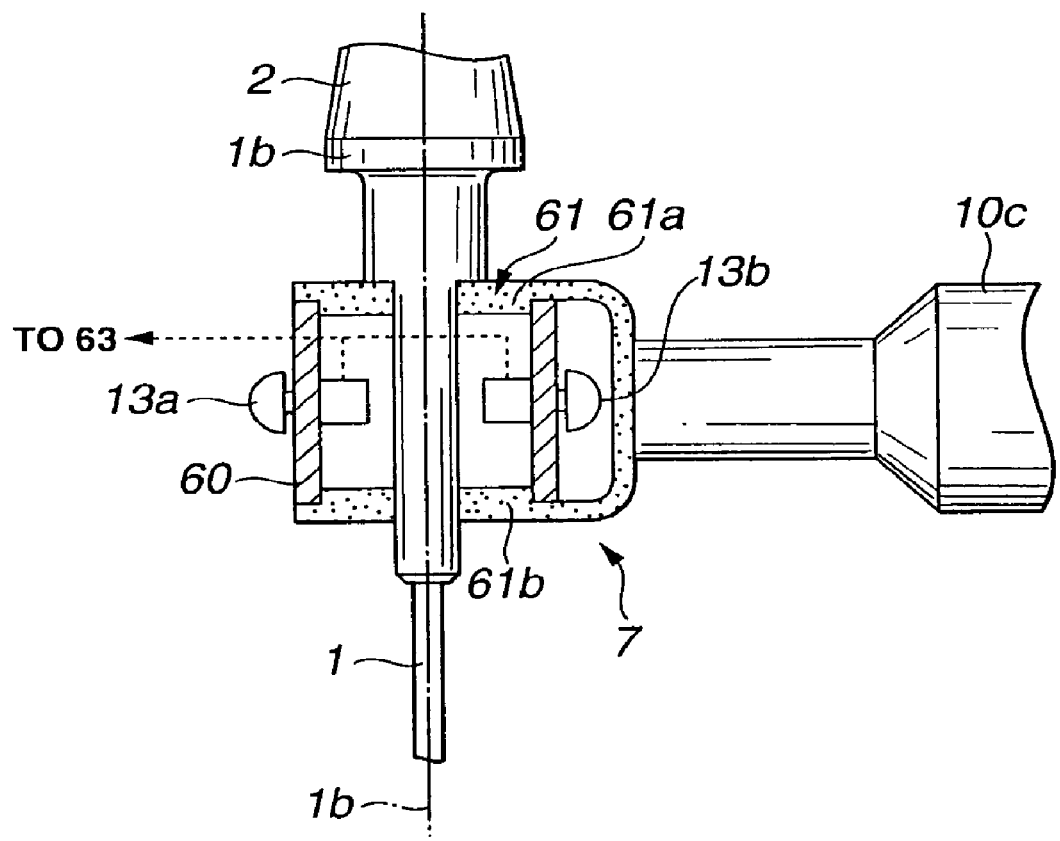

As shown in FIG. 11, the rotating member 60 has a pipe-shaped form. The rotating member 60 is fit in between cylindrical protrusion 61a and 61b of the holding member 61, and rotates freely with respect to the insertion axis 1b of the endoscope 1.

A first switch 13a and second switch 13b are provided at axially symmetrical positions as to the axis 1b of the endoscope 1, on the perimeter of the rotating member 60. The first switch 13a and second switch 13b are connected to a later-described fluid control unit denoted by reference numeral 63 in FIG. 12A, serving as fixing force control means.

Figure 12A:
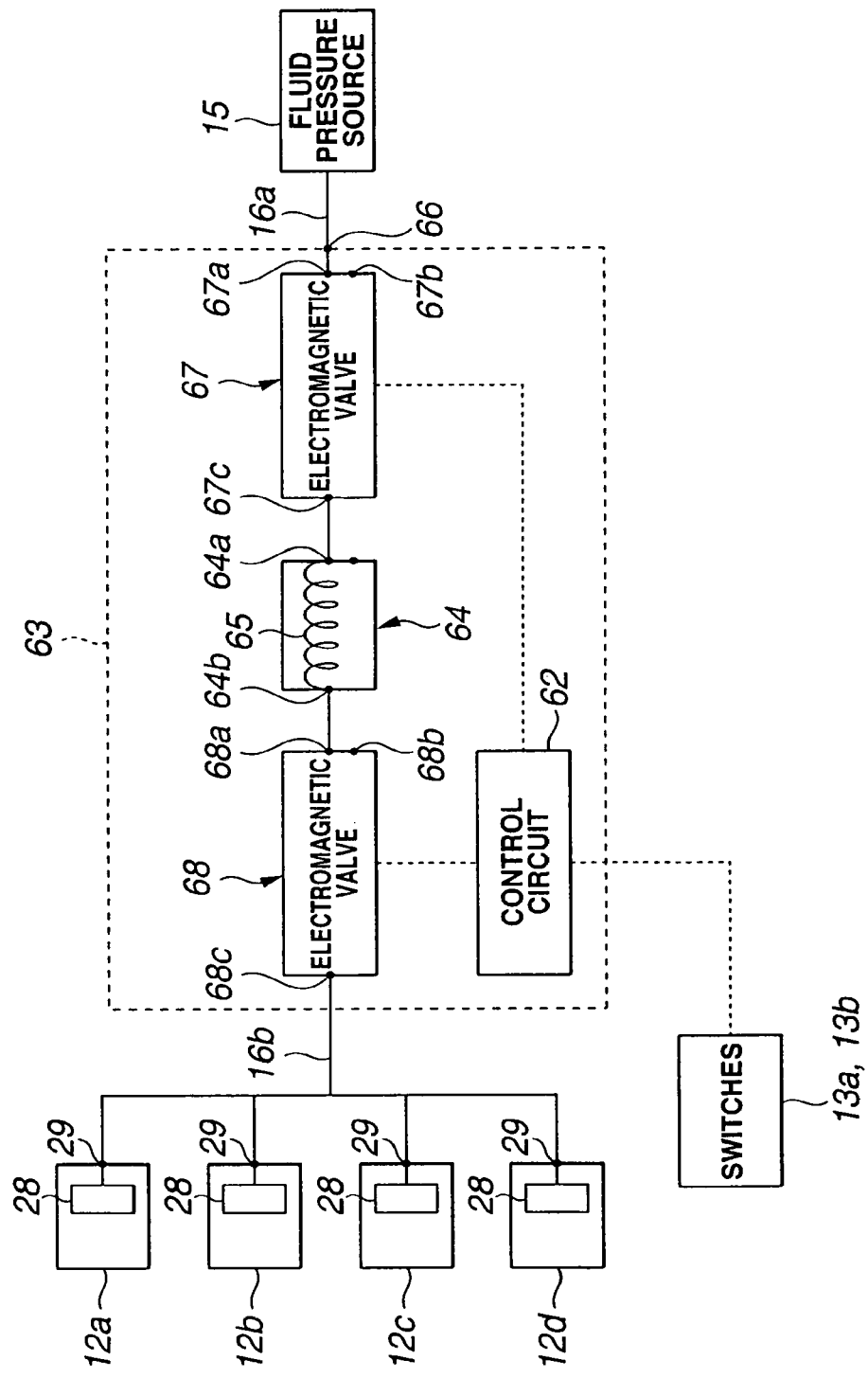
FIG. 12A is a block diagram explaining yet another configuration of the surgery equipment holding device.

As shown in FIG. 12A, the fluid control unit 63 comprises a control circuit 62, a first electromagnetic valve 67 and second electromagnetic valve 68 similar to the electromagnetic valve 30 in the first embodiment, and a fluid transmission delay unit 64.

The first switch 13a and second switch 13b are electrically connected to the electromagnetic valves 67 and 68 respectively via the control circuit 62. The fluid transmission delay unit 64 comprises ports 64a and 64b which are inlet/outlets for the fluid, with a long hose 65 of which tube length is long coupled. The long hose 65 is airtight and capable of passing fluid between the ports 64a and 64b.

The tube length of the hose 65 is set to that capable of exhibiting the later-described operations in comparison with the above-described hose 16b, specifically.

The fluid pressure source 15 is coupled via the hose 16a to the input port 66 of the fluid control unit 63, such that the connection is airtight, while allowing the fluid to pass through. The input port 66 and the input port 67a of the first electromagnetic valve 67 are coupled such that the connection is airtight, while allowing the fluid to pass through. The functional port 67c of the first electromagnetic valve 67 and the port 64a of the fluid transmission delay unit 64 are coupled such that the connection is airtight, while allowing the fluid to pass through.

Also, the port 64b of the fluid transmission delay unit 64 and the input port 68a of the second electromagnetic valve 68 are coupled such that the connection is airtight, while allowing the fluid to pass through. Moreover, the functional port 68c of the second electromagnetic valve 68 and the hose 16b are coupled such that the connection is airtight, while allowing the fluid to pass through.

The branched base of the hose 16b is coupled in parallel to the inlet port 29 of the airtight space 28 formed at the first fluid brake 12a, second fluid brake 12b, third fluid brake 12c, and fourth fluid brake 12d, such that the connection is airtight, while allowing the fluid to pass through. Also, the discharge ports 67b and 68b of the electromagnetic valves 67 and 68 are opened to the atmosphere.

The operation of the surgery equipment holding device thus configured will now be described.

In the state that the surgeon has not pressed the first switch 13a and second switch 13b, the functional port 67c and discharge port 67b of the electromagnetic valve 67, and the functional port 68c and discharge port 68b of the electromagnetic valve 68 communicate. Accordingly, the airtight space 28 within the first fluid brake 12a, second fluid brake 12b, third fluid brake 12c, and fourth fluid brake 12d, and the interior of the hose 65 of the fluid transmission delay unit 64, are opened to the atmosphere. Thus, as with the first embodiment, the first fluid brake 12a, second fluid brake 12b, third fluid brake 12c, and fourth fluid brake 12d, are in a fixed state.

In the event of moving the endoscope 1, the surgeon presses and operates the first switch 13a and second switch 13b. This causes the electromagnetic valves 67 and 68 within the fluid control unit 63 to operate in the same manner as with the first embodiment, via the control circuit 62. That is to say, the input port 67a and the functional port 67c of the electromagnetic valve 67 communicate, and the input port 68a and the functional port 68c of the electromagnetic valve 68 communicate.

Thus, the pressured fluid starts to flow in from the fluid pressure source 15. The pressured fluid then passes through the hose 65 disposed at the fluid transmission delay unit 64, and increases the pressure inside the airtight space 28 within the first fluid brake 12a, second fluid brake 12b, third fluid brake 12c, and fourth fluid brake 12d. As a result of this, the first fluid brake 12a, second fluid brake 12b, third fluid brake 12c, and fourth fluid brake 12d attain a fixation disengaged state, as with the first embodiment.

Then, when the surgeon releases the first switch 13a and the second switch 13b to fix the endoscope 1, the first switch 13a and the second switch 13b make transition to the original state before being operated.

Consequently, the pressured fluid filling the airtight space 28 is discharged into the atmosphere from the discharge port 68b of the second electromagnetic valve 68. On the other hand, the pressured fluid filling the hose 65 of the fluid transmission delay unit 64 is discharged into the atmosphere from the discharge port 67b of the first electromagnetic valve 67.

That is to say, the pressured fluid within the airtight space 28 must pass through the hose 65 of the fluid transmission delay unit 64 in the event that the surgeon moves the endoscope 1, but does not pass through the hose 65 in the event that the surgeon fixes the endoscope 1.

Accordingly, the longer the hose 65 is, the longer the time required for the pressured fluid to pass through the hose 65. Thus, when comparing the amount of change in pressure in the airtight space 28 per time increment for the first fluid brake 12a, second fluid brake 12b, third fluid brake 12c, and fourth fluid brake 12d to make transition to the disengaged state or the fixed state from the time of pressing or releasing the first switch 13a and the second switch 13b, the amount of change in pressure is clearly smaller at the time of disengaging the fixation than at the time to the fixed state.

This means that, as with the above-described embodiments, the disengaging action of the surgery equipment holding device can be carried out gradually, while the fixing action of the surgery equipment holding device can be performed rapidly.

Also, providing the switches at axially symmetrical positions as to the insertion axis of the endoscope obtains the same operations as with the third embodiment. Further, with the present embodiment, the switches are rotatable with respect to the insertion axis of the endoscope, so in the event that the position is such that the surgeon cannot readily press the switches, rotating the rotating member allows rotation with the relative positional relation maintained between the switches and the endoscope. Thus, the surgeon can change the position of the switches to an easily-operated position, thereby reducing fatigue of the surgeon and improving the efficiency of the surgery.

Figure 12B:
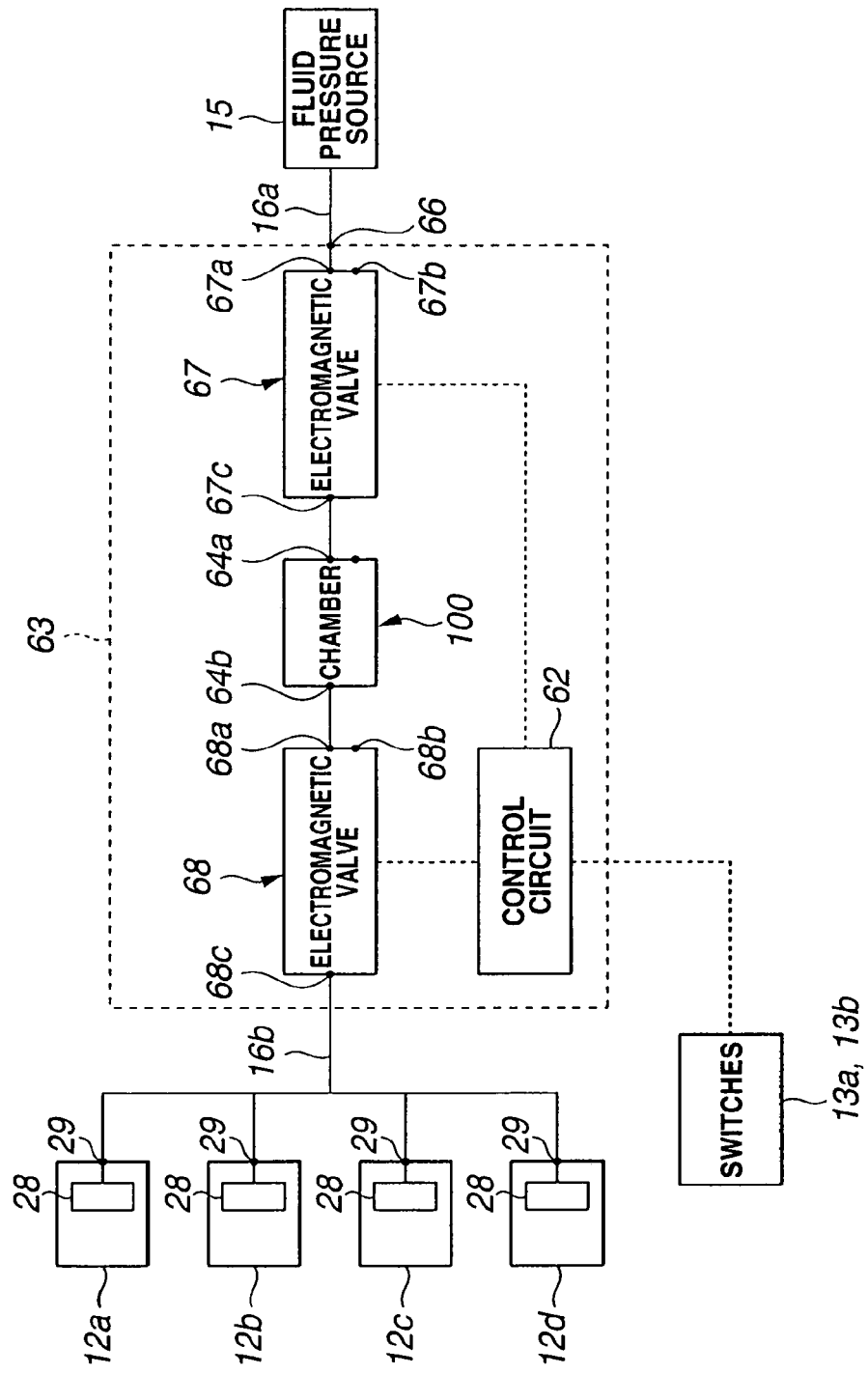

Also, though the present embodiment has been described with a configuration using a hose for the fluid transmission delay unit, the same operations and advantages can be obtained with other arrangements, such as replacing the fluid transmission delay unit with a container such as a chamber 100 shown in FIG. 12B, or the diaphragm 39 and variable diaphragm 39a shown in FIGS. 4A and 4B.

A fifth embodiment of the present invention will be now described with reference to FIGS. 13 to 14B.

The configuration of the present embodiment is an arrangement wherein the control unit of the second embodiment disclosed in Japanese Unexamined Patent Application Publication No. 07-227398 mentioned above as conventional art is replaced with a later-described control circuit 70.

Figure 13:
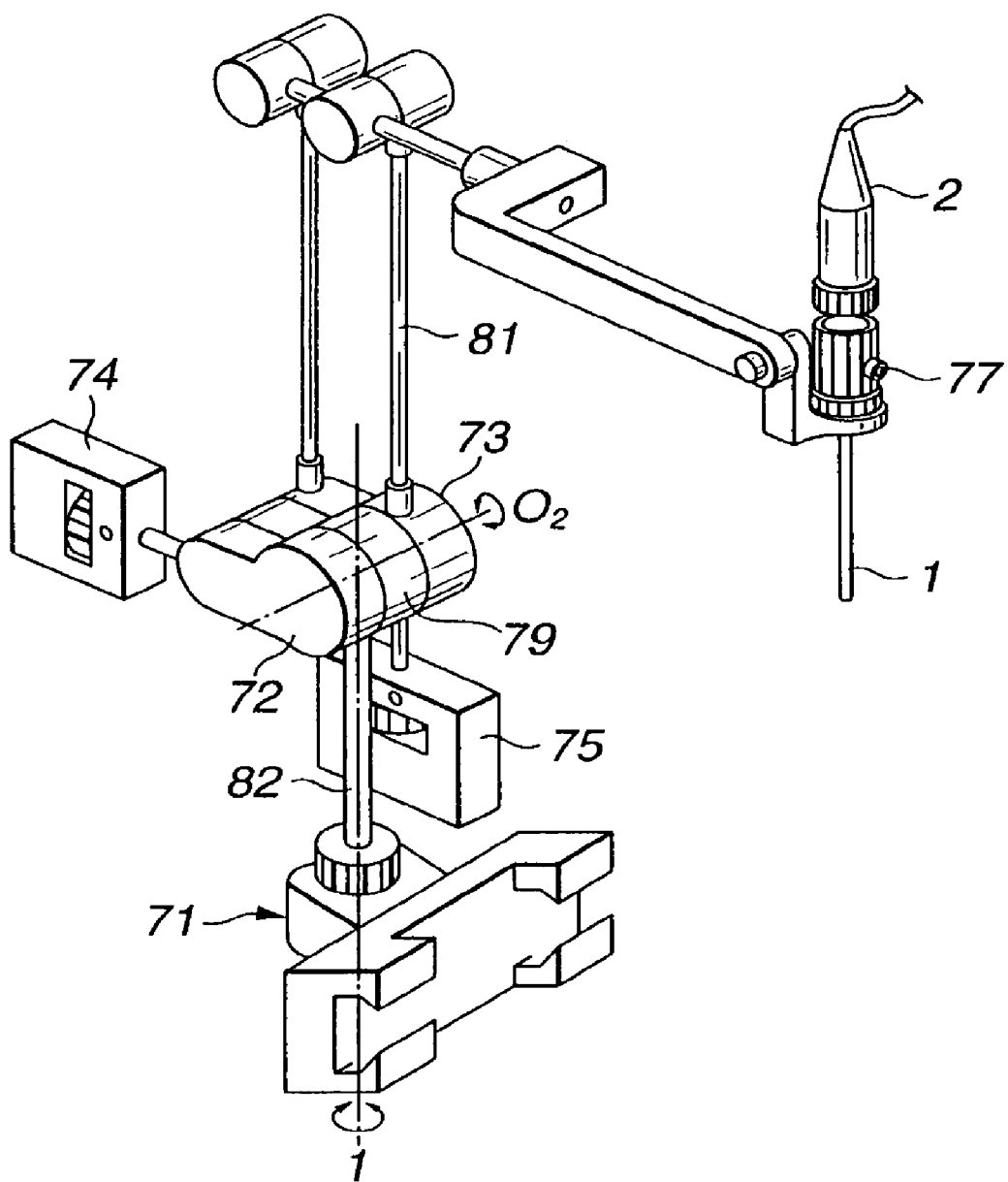

As shown in FIG. 13, the surgery equipment holding device comprises electromagnetic brakes 71, 72, and 73, and counterweights 74 and 75. In the event that the fixation state of the joints disposed on the arm portion is disengaged, the endoscope 1 maintains a balanced state by the counterweights 74 and 75.

Figure 14A:
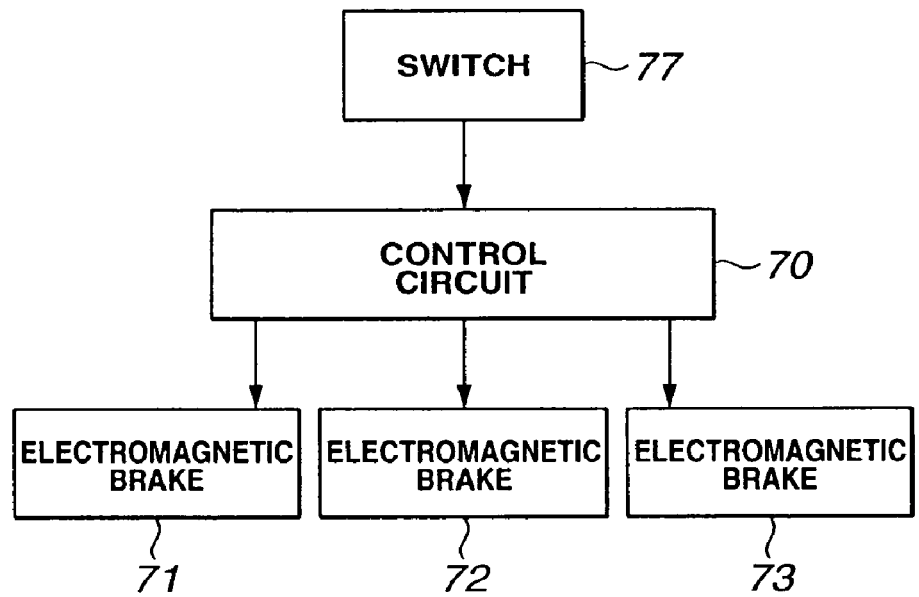
FIG. 14A is a block diagram explaining the position where the control circuit is disposed.

As shown in FIG. 14A, the control circuit 70 serving as fixing force control means in the present embodiment is electrically connected and disposed between a switch 77 and the electromagnetic brakes 71, 72, and 73.

The functional configuration of the control circuit 70 is such that, in the event that the switch 77 is pressed, the voltage increases as to the electromagnetic brakes 71, 72, and 73, at a predetermined voltage increase per time increment, dE (V/sec). On the other hand, in the event that the switch 77 is turned off, the voltage decreases at a predetermined voltage decrease dEs (V/sec).

The present embodiment sets the relation $dE \leq dEs$ between dE and dEs in the present embodiment, so as to effect control.

Figure 14B:
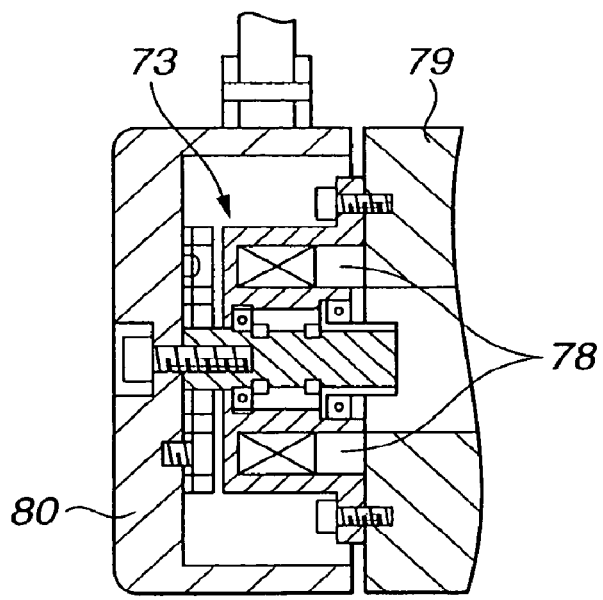

Further, with the present embodiment, in the event that the switch 77 is not operated, the electromagnetic brakes 71, 72, and 73 are fixed by a magnetic force P0 due to a permanent magnet 78 as shown in FIG. 14B.

Upon the surgeon grasping the grasping portion of the endoscope and pressing the switch 77, voltage is applied to the electromagnetic brakes 71, 72, and 73 increasing by dE (V/sec). Accordingly, the fixation state is gradually disengaged.

Then, when the surgeon releases the switch 77, the control circuit 70 immediately shuts off electric power supply to the electromagnetic brakes 71, 72, and 73. Subsequently, the voltage is decreased by dEs (V/sec) per time increment.

In other words, with the control circuit 70, the electromagnetic brakes gradually operate to disengage the fixing force thereof in the event that the surgeon presses the switch 77 to move the endoscope 1, due to the setting of the relation $dE \leq dEs$ between the amount of voltage increase and the amount of voltage decrease. Thus, the same operations and advantages as with the above embodiments can be obtained.

Accordingly, with the present embodiment, the desired operations and advantages can be easily realized by adding this control circuit to the surgery equipment holding device using known electromagnetic brakes.

Also, situations wherein force of the hand of the surgeon is suddenly applied to the surgery equipment holding device at the time of disengaging braking, which may occur even with balanced surgery equipment holding devices, can be avoided with the present embodiment, meaning that the surgeon can perform fixation disengaging operation of the surgery equipment without losing sight of the part to be treated or observed with the surgery equipment, and also can quickly perform fixing operations, as well.

Now, FIG. 15 is a diagram explaining a modification of the fifth embodiment. As shown in FIG. 15, with the present embodiment, motor brakes 90 are used instead of the electromagnetic brakes 71, 72, and 73 in the fifth embodiment.

The motor brakes denoted by reference numeral 90 in the figure are motor brakes using known motors, and in the present embodiment the motor brakes 90 are disposed instead of the electromagnetic brakes 71, 72, and 73 in FIG. 13.

Here, description will be made regarding the motor brake 90 disposed at a lock of a swinging rod 81, and description of the remaining motor brakes will be omitted since the configuration thereof is the same.

A cover 80 is rotatably disposed so as to rotate on a rotating axis O2 as the axis thereof, by bearings 91a and 91b disposed on a supporting member 79 disposed on the upper part of a vertical rod 82. The lower end of the swinging rod 81 is linked to the cover 80.

Reference numeral 92 denotes a motor, which is electrically connected to the switch 77 via the control circuit 70. The motor 92 is integrally fixed to an internal tube 94 by a screw 93. Also, the internal tube 94 and the supporting member 79 are integrally fixed by a screw 95.

An operating screw 97 is rotatably disposed by bearings 96a and 96b within an internal tube 94. This operating screw 97 is integrally joined to a rotational output shaft 92a of the motor 92.

At the time of disengaging fixation, the control circuit 70 runs the motor 92 at a rotation speed R (rpm), and at the time of fixing, runs the motor 92 at a rotation speed Rs (rpm). The present embodiment sets the relation of $R \ll Rs$ between the rotation speed R and the rotation speed Rs, thereby effecting control.

Also, reference numeral 98 denotes a lock nut, wherein female threads for screwing the operating screw 97 to are formed on the inner face of the lock nut 98, and a spline 98a is formed on the perimeter face thereof.

A spline 79a capable of sliding with the spline 98a is formed on the end of the internal circumference of the supporting member 79 at the cover 80 side. Thus, rotation of the lock nut 98 in the direction of rotating around the rotational axis O2 is suppressed, while being slidable parallel to the rotational axis O2.

Reference numeral 98b denotes a pressing portion for pressing the internal face of the cover 80, that has been formed on the end of the lock nut 98.

Now, the operation of the surgery equipment holding device will be described, including the operations of the motor brake.

In the state that the cover 80 and the supporting member 79 are pressed and fixed by the pressing portion 98b formed on the end of the lock nut 98, the surgeon pressing the switch 77 causes the control circuit 70 to run the motor 92. The resultant rotating action of the rotating output shaft 92a starts rotation of the operating screw 97 which has been joined to the rotating output shaft 92a and is screwed to the lock nut 98.

At this time, the rotation of the lock nut 98 is suppressed by the spline 98a and 79a. Accordingly, the lock nut 98 moves parallel to the rotational axis O2 in the direction of the arrow, and disengages the pressed state by the pressing portion 98b. As a result, the cover 80 and the supporting member 79 become rotatable on the rotational axis O2.

Subsequently, in the event that the surgeon releases the switch 77, the control circuit 70 starts the motor 92 rotating in the direction opposite to that described above. Accordingly, action opposite to that described above causes the lock nut 98 to move parallel to the rotational axis O2 in the direction opposite to that described above, so that the pressing portion 98b is in the pressing state again, and the cover 80 and the supporting member 79 are in the fixing state again.

Now, the rotation of the motor 92 is made by the control circuit 70 to be slower when fixation is disengaged as compared to when fixed, so the action of disengaging the surgery equipment that is held can be carried out gradually, while the fixing action can be performed rapidly, so the surgeon can work without losing sight of the part to be treated or observed with the surgery equipment In this way, according to the present configuration, the control of the fixing force is control of only the rotation speed of the motor, so electrical control can be performed even more easily.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A surgery equipment holding device, comprising:
   a holder for holding surgery equipment;
   a bar connected to the holder;
   a brake for operatively engaging the bar to stop movement of the bar;
   a control unit that is adapted to provide an inactivation lead time for rendering the brake inactive being longer than an activation lead time for making the brake active, the control unit comprising a control circuit, the control circuit providing a voltage increase per time and a voltage decrease per time to the brake, wherein the voltage increase per time is less than the voltage decrease per time; and
   a switch for switching the brake between an active state and an inactive state; wherein an electric power source for generating electric power; and the control circuit for controlling the amount of change of electric power supplied from the electric power source in a time increment, according to switching of the switch; wherein the brake is a motor brake which operates according to electric power supplied from the electric power source.

2. The surgery equipment holding device according to claim 1,
   wherein the brake is an electromagnetic brake which operates according to electric power supplied from the electric power source.

* * * * *